US011646114B2

(12) United States Patent
Gabriel et al.

(10) Patent No.: US 11,646,114 B2
(45) Date of Patent: May 9, 2023

(54) METHOD AND SYSTEM FOR PROCESSING OF ELECTRONIC MEDICAL INVOICES

(71) Applicant: SAP SE, Walldorf (DE)

(72) Inventors: Jan Gabriel, Walldorf (DE); Torsten Born, Walldorf (DE)

(73) Assignee: SAP SE, Walldorf (DE)

(*) Notice: Subject to any disclaimer, the term of this patent is extended or adjusted under 35 U.S.C. 154(b) by 1117 days.

(21) Appl. No.: 15/247,961

(22) Filed: Aug. 26, 2016

(65) Prior Publication Data

US 2018/0060505 A1    Mar. 1, 2018

(51) Int. Cl.
| | |
|---|---|
| *G16H 10/60* | (2018.01) |
| *G06Q 10/10* | (2023.01) |
| *G06Q 30/04* | (2012.01) |
| *G06Q 50/22* | (2018.01) |
| *G16H 40/63* | (2018.01) |
| *G06Q 30/0601* | (2023.01) |
| *G06Q 20/10* | (2012.01) |

(Continued)

(52) U.S. Cl.
CPC ............ *G16H 40/63* (2018.01); *G06Q 10/10* (2013.01); *G06Q 20/047* (2020.05); *G06Q 20/0855* (2013.01); *G06Q 20/102* (2013.01); *G06Q 20/227* (2013.01); *G06Q 20/389* (2013.01); *G06Q 20/3821* (2013.01); *G06Q 30/04* (2013.01); *G06Q 30/0601* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 7,765,549 B1 * | 7/2010 | Lauer .................... | G06F 9/5005 707/705 |
| 9,058,515 B1 * | 6/2015 | Amtrup .................. | H04N 1/387 |

(Continued)

FOREIGN PATENT DOCUMENTS

| | | | | |
|---|---|---|---|---|
| WO | WO-2015/073920 A1 | | 5/2015 | |
| WO | WO-2015069409 A1 * | | 5/2015 | ........... G06F 19/328 |

OTHER PUBLICATIONS

Shadi AlZubi et al., Multi-Resolution Analysis Using Curvelet and Wavelet Transforms for Medical Imaging, 2011 IEEE International Symposium on Medical Measurements and Applications (2011), https://ieeexplore.ieee.org/stamp/stamp.jsp?tp=&arnumber=5966687 (Year: 2011).*

(Continued)

*Primary Examiner* — Jason B Dunham
*Assistant Examiner* — Nicholas Akogyeram, II

(57) ABSTRACT

An electronic payment system, a computer-implemented method, and a computer readable medium having stored thereon a computer executable program code for processing of the electronic medical invoices and reimbursement of medical costs is disclosed herein. The electronic payment system comprises a server operable for execution of an application management component and a set of server applications comprising receiver applications and processing applications, wherein the server comprises a processing unit and a memory storing computer executable code which when executed by the processing unit cases the server to execute the computer-implemented method.

19 Claims, 4 Drawing Sheets

(51) Int. Cl.
*G06Q 20/38* (2012.01)
*G06Q 20/22* (2012.01)
*G06Q 20/08* (2012.01)
*G06Q 20/04* (2012.01)

(56) References Cited

U.S. PATENT DOCUMENTS

| | | | | |
|---|---|---|---|---|
| 2002/0035488 A1* | 3/2002 | Aquila | ............... | G06Q 50/24 705/4 |
| 2003/0093301 A1* | 5/2003 | Chesney | ............... | G06F 19/328 705/3 |
| 2003/0153994 A1* | 8/2003 | Jin | ............... | G06Q 10/10 700/99 |
| 2003/0200118 A1* | 10/2003 | Lee | ............... | G07F 7/1008 705/2 |
| 2005/0075979 A1* | 4/2005 | Leavitt | ............... | G06Q 30/04 705/40 |
| 2010/0195894 A1* | 8/2010 | Lohweg | ............... | G07D 7/2016 382/135 |
| 2011/0078098 A1* | 3/2011 | Lapir | ............... | G06F 16/35 707/723 |
| 2011/0321058 A1* | 12/2011 | Schmidt | ............... | G06F 9/505 718/105 |
| 2012/0022887 A1 | 1/2012 | Chiappe | | |
| 2012/0228877 A1 | 9/2012 | Samuel | | |
| 2013/0046823 A1* | 2/2013 | Mitchell | ............... | G06Q 30/0201 709/204 |
| 2014/0012742 A1 | 1/2014 | Hanson et al. | | |
| 2014/0153787 A1* | 6/2014 | Schmidtler | ............... | H04N 1/40 382/112 |
| 2016/0275252 A1* | 9/2016 | Anderson | ............... | G06Q 10/103 |

OTHER PUBLICATIONS

European Office Action dated Dec. 21, 2016 and issued in corresponding European Application No. 16185959.0-1955.
European Office Action corresponding to European Application No. 16 185 959.0-1217.

\* cited by examiner

METHOD AND SYSTEM FOR PROCESSING OF ELECTRONIC MEDICAL INVOICES

TECHNICAL FIELD

This invention relates to processing of electronic medical invoices and reimbursement of medical costs related thereto. In particular, this invention relates to an electronic payment system and a computer-implemented method for reimbursement of medical costs.

BACKGROUND

Effective processing of electronic documents is an everlasting problem of a health care sector. Health insurance providers (e.g. insurance companies) process millions invoices and other related documents sent by their clients. Invoices can have different formats. Some invoices can be in electronic form, comprising data text format. Other invoices can be images of invoices printed on paper. In addition different health care institutions can have different formants of invoices. Processing of invoices can be performed in conjunction with other data. For instance a client can get extra bonus when an overall sum of medical costs reimbursed by an insurance company in a particular interval of time (e.g. a year) is below a certain limit. In addition or as alternative a client can get extra bonus when he provides health care information to the insurance company. The health care information can be related to his compliance with the health care plan determined by an insurance company. The health care information can be related to visits of fitness facilities. As a result thereof of the electronic payment system has to process a lot of heterogeneous data received from different sources.

SUMMARY

The disclosure generally describes computer-implemented methods, computer-readable media, and electronic payment system for reimbursement of medical costs. The electronic medical invoices can be received in different formats. Some of invoices can be received in electronic text format; some other invoices can be received as images of medical invoices printed on a substrate (e.g. paper). The electronic medical invoices of a user can be processed in conjunction with other information provided by the user, e.g. information related to his compliance with the health care plan. Information related to reimbursement of medical costs of a user can be received by the electronic payment system without preprocessing or any preparation, e.g. the user can simply send a photo of the medical invoice via one communication channel to the electronic payment system. The heterogeneous information related to processing of a medical invoice can be received via different communication channels by the electronic payment system. This way of data processing can enable utilization of simple computer systems like mobile phones for providing information related to reimbursement of medical costs. Effective processing of heterogeneous information received via different communication channels is provided by configurable pipeline processing executed on the electronic payment system. The configurable pipeline processing is implemented by constructing different pipelines using a plurality of applications executed on the electronic payment system. Different pipelines for processing of data of specific types can be configured as a sequence of applications, wherein every next application in the sequence processes data received from an application being in the sequence immediately before the every next application the sequence. High degree of customization of the applications for execution of specific operations in conjunction with flexible construction of sequences enabling simultaneously using one application in different sequences can provide not only for effective processing of electronic medical invoices but for effective utilization of hardware resources of the electronic payment system.

More than one application in the sequence can be configured to receive data. This feature can simplify processing of the heterogeneous information. For instance the first application in a sequence of applications can receive electronic medical invoices of a user. One of the next applications in this sequence can be configured to receive costs of the user extracted from the received medical invoices by an application being in the sequence before the one of the next applications the sequence. The one of the next applications can be further configured to calculate the amount to be reimbursed in conjunction with data related to compliance of the user with his healthcare plan. Adding info related to the compliance with the health care plan at this stage of processing can be very effective, because further configuring a portion of the sequence of applications which is configured to receive medical invoices of the user and to provide costs of the user extracted from the medical invoices, can be counterproductive because this will require customization of said portion of the sequence for additional workload like processing of info related to the compliance with the healthcare plan, i.e. customization for processing of heterogeneous data. The latter can be incompatible with paradigm of customization of an application for execution of a specific operation on data of a specific type.

It is an objective of embodiments of the invention to provide for a system configured to provide effective processing of electronic medical invoices, a computer-implemented method for effective processing of electronic medical invoices, and a computer readable medium having stored thereon a computer executable program code for effective processing of electronic medical invoices. Advantageous embodiments are described in the dependent claims.

According to one embodiment, the present invention relates to an electronic payment system for reimbursement of medical costs. The system comprises a server operable for execution of an application management component and a set of server applications comprising receiver applications and processing applications. The server comprises a processing unit and a memory storing computer executable code which when executed by the processing unit cases the server to execute the following: the server receiving via a digital cellular telecommunication network an electronic medical invoice from a sender application executed on an end terminal; the application management component assigning a sequence of the server applications of the set of server applications for processing of electronic medical invoices, wherein an application being the first in the sequence is a receiver application configured to receive and to process the electronic medical invoice, wherein each next following server application in the sequence is configured to process further the electronic medical invoice previously processed by the server application being in the sequence immediately before the each next following server application in the sequence, wherein the last server application in the sequence is configured to execute reimbursement of medical costs according to the electronic medical invoice processed by the server applications of the sequence of the applications; and the application management component causing the sequence of the server applications to process the electronic medical invoice.

According to another embodiment, the present invention relates to a computer-implemented method for reimbursement of medical costs using an electronic payment system comprising a server operable for execution of an application management component and a set of server applications comprising receiver applications and processing applications. The computer-implemented method comprises the following: the server receiving via a digital cellular telecommunication network an electronic medical invoice from a sender application executed on an end terminal; the application management component assigning a sequence of server applications of the set of server applications for processing of electronic medical invoices, wherein an application being the first in the sequence is a receiver application configured to receive and to process the electronic medical invoice, wherein each next following server application in the sequence is configured to process further the electronic medical invoice previously processed by the server application being in the sequence immediately before the each next following server application in the sequence, wherein the last server application in the sequence is configured to execute reimbursement of medical costs according to the electronic medical invoice processed by the server applications of the sequence of the applications; and the application management component causing the sequence of the server applications to process the electronic medical invoice.

According to another embodiment, the present invention relates to a computer readable medium having stored thereon a computer executable code for execution by a computer processor controlling an electronic payment system, wherein execution of instructions of the executable code causes by the computer processor causes the computer processor to execute the computer-implemented method of the aforementioned embodiment.

These embodiments can be advantageous because they can enable effective utilization of server applications, wherein each of the server applications is configured and/or customized for execution of a specific operation on the electronic medical invoice. The digital cellular telecommunication network in the aforementioned embodiments and further in the detailed description can be but is not limited to: GSM (Global System for Mobile Communications), GRPS (General Packet Radio Service), UMTS (Universal Mobile Telecommunications System), and LTE (Long Tern Evolution).

The details of one or more implementations of the subject matter of this specification are set forth in the accompanying drawings and the description below. Other features, aspects, and advantages of the subject matter will become apparent from the description, the drawings, and the claims.

DETAILED DESCRIPTION

Figure 1:
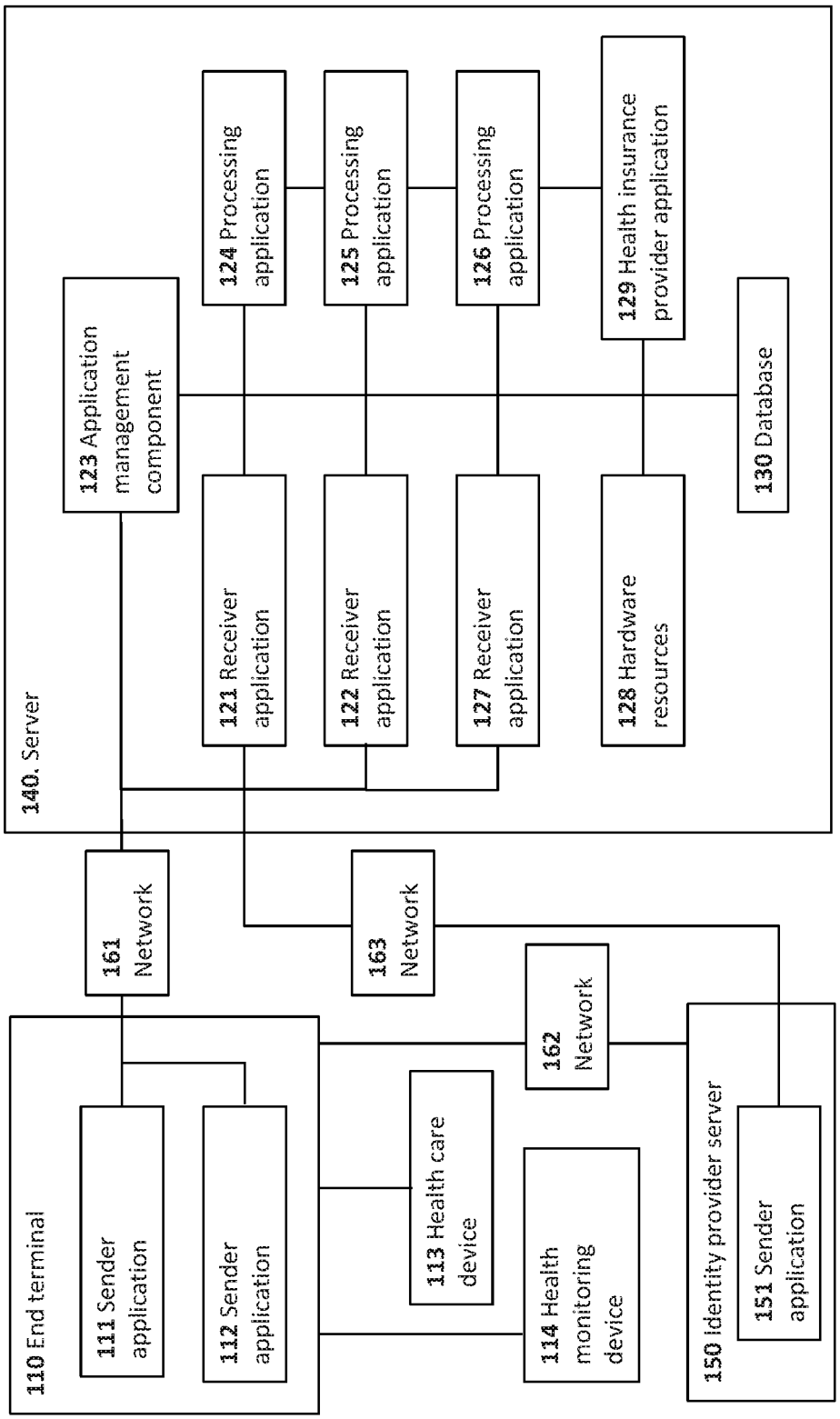
FIG. 1 is a block diagram illustrating an example environment for processing of electronic medical invoices.

This disclosure generally describes computer-implemented methods, computer-readable media, and computer systems for processing electronic medical invoices. The electronic medical invoices can be electronic data in various formats. Electronic medical invoices can be formulated as E-Mails. Other electronic medical invoices can electronic documents be attached to E-Mails (e.g. documents in pdf format). Yet other electronic medical invoices can be images of medical invoices printed on a carrier (e.g digital photo of a medical invoice printed on paper). The following description is presented to enable any person skilled in the art to practice the disclosed subject matter, and is provided in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described and/or illustrated implementations, but is to be accorded the widest scope consistent with the principles and features disclosed herein.

According to another embodiment of the present invention, each electronic medical invoice has a respective type. The application management component is configured to assign a respective customized sequence of the server applications of the set of the server applications for processing of each of the types. The sequence of the server applications in the aforementioned embodiment is one of the customized sequences of the server applications. At least two of the customized sequences of the server applications have common fragments of the sequences of the server applications. Each of the customized sequences of the server applications begins with the respective receiver application for receiving and processing of the electronic medical invoices of the type for which the each of the customized sequences of the server applications is customized. The electronic medical invoices of one type are the electronic medical invoices having a text format. The electronic medical invoices of another type comprise images of medical invoices printed on carriers (e.g. paper). The electronic medical invoices of each of the types are received via digital cellular telecommunication networks by the server from respective sender applications for sending the electronic medical invoices of the each of the types.

This embodiment can be advantageous because it can provide for an optimum balance between customization of the sequences and an overall number of server applications, because some of the sequences can comprise the same server applications. When the latter was not the case an overall number of server applications could have been higher, because in this case each of the customized sequences was constructed out of the server applications used only in the each of customized sequences.

According to another embodiment of the present invention each electronic medical invoice has a respective type. The application management component is operable for monitoring a number of electronic medical invoices to be processed by the server applications of the sequence of the server applications. One or more of the server applications of the sequence of the server applications are configured to process the electronic medical invoices in two modes, wherein in one mode of the two modes the electronic medical invoices are processed one by one and in another one of the two modes the electronic medical invoices of the same type are processed batch wise. The execution of the executable code by the processing unit cases the server to execute the following: the application management component causing the server application to process electronic medical invoices in the another one of the two modes when a number of electronic medical invoices of the same type to be processed by said server application is bigger than a predefined number otherwise the application management component causing said server application to process the electronic medical invoices in the one of the two modes.

This embodiment can be advantageous because it can provide for optimization of the workload of the server application and as a result thereof improve processing efficiency of the sequence of the server applications.

According to another embodiment of the present invention the application management component is operable for monitoring a work load of the server application of the sequence of the server applications. The application management component is operable for allocating of hardware resources of the server for execution of the server applications. The execution of the executable code by the processing unit cases the server to execute the following: the application management component allocating respective hardware resources of the server for execution of each of the server applications of the sequence of the server applications in conjunction with the respective work load of the each of the server application of the sequence of the server applications such that time required for processing of electronic medical invoices by the sequence of the server applications is minimized.

This embodiment can be advantageous, because it can provide for optimum allocation of the hardware resources. The hardware resources can be allocated in a way enabling effective processing of the electronic medical invoices.

According to another embodiment of the present invention the server comprises a database. A processing application of the sequence of server applications is operable for monitoring and managing work load of said processing application. The execution of the executable code by the processing unit cases the server to execute the following: said processing application splitting in two portions a set of electronic medical invoices to be processed by it when a number of the electronic medical invoices of the set exceeds a predefined number; said processing application storing in the database one of the two portions; said processing application processing another one of the two portions; said processing application retrieving from the database the one of the two portions; and said processing application processing the one of the two portions retrieved from the database after the another one of the two portions is processed by said processing application.

This embodiment can be advantageous because it can provide for extra flexibility of the sequence of the server applications. The database can function as a cache for optimization of the workload of the server application of the sequence.

According to another embodiment of the present invention, each electronic medical invoice is assigned to a respective user. The application management component is operable for configuring the server applications to process electronic medical invoices according to user specific rules. The execution of the executable code by the processing unit cases the server to execute the following: the application management component receiving from an application of a health insurance provider a user specific rule assigned to a user; and the application management component configuring a processing application of the sequence of the server applications to process the electronic medical invoices assigned to said user according to the received user specific rule.

This embodiment can be advantageous because it can provide for extra flexibility/functionality of the sequence of the server applications.

According to another embodiment of the present invention, the execution of the reimbursement of medical costs according to the electronic medical invoice processed by the server applications of the sequence of the server applications comprises sending information for the reimbursement of the medical costs to the application of the health insurance provider. The application of the health insurance provider is operable for updating user specific rules on a basis of the information for the reimbursement of the medical costs. The execution of the executable code by the processing unit cases the server to execute the following: the application of the health insurance provider receiving the information for the reimbursement of the medical costs; the application of the health insurance provider updating said user specific rule on the basis of the information for the reimbursement of the medical costs in response to the receiving of the information for the reimbursement of the medical costs; and the application management component receiving the updated user specific rule from the application of the health insurance provider.

This embodiment can be advantageous because it can provide for extra flexibility/functionality of the sequence of the server applications. The functioning of the server application in the sequence can be corrected on a basis of the processed electronic medical invoices. In the other words, this embodiment provides for an interactive feedback loop enabling changed in processing of the electronic medical invoices without modification of the sequence of the server applications as such.

According to another embodiment of the present invention, the application of the health insurance provider is executed on the server.

This embodiment can be advantageous, because it can provide for a decrease in data traffic between the server and other computer system, since application of the health insurance provider is executed on the server itself.

According to another embodiment of the present invention, the application management component is operable for configuring the server applications to process the electronic medical invoices according to user specific rules. The electronic medical invoice is assigned to a user. The end terminal is a mobile phone. The execution of the executable code by the processing unit cases the server to execute the following: the application management component receiving from an application of a health insurance provider a user specific rule assigned to the user, wherein the user specific rule determines processing of his electronic medical invoices in conjunction with his user specific information being descriptive of his compliance with his health care plan; and the application management component configuring another receiver application of the set of the server applications to perform the following: receiving the user specific information via the digital cellular telecommunication network from another sender application executed on the end terminal; converting the received user specific information in a data format being parsable by a processing application of the sequence of the server applications; and sending the converted user specific information to said processing application. The execution of the executable code by the processing unit cases the server to execute the following: the application management component configuring said processing application to perform the following: receiving from the another receiver application the converted user specific information; and executing the processing of electronic medical invoices assigned to the user in conjunction with the received converted user specific information according to the user specific rule.

This embodiment can be advantageous because, it can provide for a modification of the sequence of the server applications for processing the electronic medical invoices using additional without reconstructing the sequence of the server applications as such.

According to another embodiment of the present invention, the processing application mentioned in the previous embodiment is operable for causing the end terminal via the another sender application and the another receiver application to collect the user specific information from one or more health care devices and/or one or more health monitoring devices. The execution of the executable code by the processing unit cases the server to execute the following: the application management component causing said processing application to cause the end terminal via the another sender application and the another receiver application to collect the user specific information from the one or more health care devices and/or the one or more health monitoring devices.

This embodiment can be advantageous because, it can provide for using already established channel of communication between the server and the end terminal for obtaining additional user specific information needed for processing of the electronic medical invoices. The user can protect his privacy when he does not want to provide the user specific information just by deactivating a respective application on his end terminal.

According to another embodiment of the present invention, the electronic medical invoice is an electronic file comprising an image of a medical invoice printed on a substrate. The image is a mixed text/graphic image. One of the server applications in the sequence of the server applications is configured to extract text data from an image. The step in which the application management component causes the sequence of the server applications to process the electronic medical invoice comprises the following: the one of the server applications extracting text data from the image comprised in the electronic medical invoice. The step in which the one of the server application extracts the text data form the image comprised in the electronic medical invoice comprises the following: identifying one or more graphical objects in the image using a first pattern recognition method; generating an auxiliary image by subtracting image of the one or more graphical objects from the image; and identifying the text data in the auxiliary image using a second pattern recognition method.

This embodiment can be advantageous because, it can provide for an optimal extraction of the text data from the electronic medical invoice. It might be difficult to develop a universal pattern recognition method which can extract the text data from mixed text/graphic images. That is why using consecutive processing of the image by two pattern recognition method can make the results more reliable. The reliability of the text data is of particular importance for this application because a failure in determination of costs to be reimbursed can result in mistakes of several orders of magnitude when decimal point is in the cost number is identified in a wrong way.

According to another embodiment of the present invention, the second pattern recognition method is a statistical pattern recognition method.

This embodiment can be advantageous because, the statistical pattern recognition method can be optimized for extracting text data from images of text data.

According to another embodiment of the present invention, the first pattern recognition method comprises a feature extraction method in which features of graphical object are extracted from the image using a set of wavelet functions.

This embodiment can be advantageous, because it can provide for an optimum algorithm for recognition of the graphical objects in the image of medical invoice.

According to another embodiment of the present invention, the server comprises a database storing graphical objects each associated with a respective text fragment. The step in which the one of the server applications extracts the text data form the image comprised in the electronic medical invoice comprises the following: identifying a set of graphical objects, wherein each of the graphical objects of the set of graphical objects is stored in the database and is identified in the step of the identifying of the one or more graphical objects in the image using the first pattern recognition method; in case when the set of graphical objects is empty the one of the server applications sending an error message to the application manager component, otherwise retrieving from the database a set of text fragments, wherein each of the text fragments of the set of text fragments is associated with the respective graphical object of the set of graphical objects, wherein the identifying of the text data in the auxiliary image using the second pattern recognition method is executed when the set of graphical objects is not empty; and in case when none of the text fragments of the set of text fragments is comprised in the identified text data the one of the server applications sending the error message to the application manager component.

This embodiment can be advantageous because it can provide for a double check of correctness of the extracted text data against two different reference items stored in the database.

According to another embodiment of the present invention, the electronic medical invoice is an electronic file comprising an image of a medical invoice printed on a substrate. The image is a mixed text/graphic image. One of the server applications in the sequence of the server applications is configured to extract text data from an image. The server comprises a database storing graphical objects each associated with a respective text fragment. The database stores sets of wavelet functions. The step in which the application management component causes the sequence of the server applications to process the electronic medical invoice comprises the following: the one of the server applications extracting text data from the image comprised in the electronic medical invoice. The step in which the one of the server application extracts the text data form the image comprised in the electronic medical invoice comprises the following steps: a) identifying one or more graphical objects in the image using a first pattern recognition method, wherein the first pattern recognition method comprises a feature extraction method in which features of graphical objects are extracted from the image using one of the sets of wavelet functions; b) identifying a set of graphical objects, wherein each of the graphical objects of the set of graphical objects is stored in the database and is identified in the last execution of step b); c) in case when the set of graphical objects identified in the last execution of step b) is empty repeating steps a) and b) until the set of graphical objects identified in the last execution of step b) is not empty or all sets of the wavelet functions stored in the database are used in step a), wherein in every next repetition of step a) another not yet used in step a) set of wavelet functions stored in the database is used; d) in case when the set of graphical objects identified in the last execution of step b) is not empty performing the following: retrieving from the database a set of text fragments, wherein each of the text fragments of the set of text fragments is associated with the respective graphical object of the set of graphical objects identified in the last execution of step b); generating an auxiliary image by subtracting from the image an image of the one or more graphical objects identified in the last execution of step a); and identifying, using a second pattern recognition, text data in the auxiliary image which is generated in the last execution of the step of the generating an auxiliary image by subtracting from the image an image of the one or more graphical objects identified in the last execution of step a); e) in case when none of the text fragments of the set of text fragments retrieved from the database in the last execution of step d) is comprised in the text data identified in the last execution of step d) repeating steps a)-d) until one of the text fragments of the set of text fragments retrieved from the database in the last execution of step d) is comprised in the text data identified in the last execution of step d) or all sets of the wavelet functions stored in the database are used in step a), wherein in every next repetition of step a) another not yet used in step a) set of wavelet functions stored in the database is used, wherein the text data extracted by the one of the server applications from the image comprised in the electronic medical invoice is the text data identified in step d) when one of the text fragments of the set of text fragments is comprised in the text data identified in step d).

This embodiment can be advantageous because it can provide for a process with iterative optimization of algorithm and multiple control of correctness of the identified graphical objects and the identified text data.

According to another embodiment of the present invention, the graphical objects stored in the database are logotypes of health care providers and the text fragments are company details of the health care providers, wherein the logotype of each of the health care providers is associated in the database with the company details of the each of the health care providers.

This embodiment can be advantageous because it can provide for a set of a priori known set of graphical objects each associated with the respective text fragment which is used for verification of correctness of extracted text data.

According to another embodiment of the present invention, the execution of the executable code by the processing unit cases the server to execute the following: the application management component executing the following in response to receiving the error message from the one of the server applications: aborting execution of the step in which the one of the server application extracts text data form the image comprised in the electronic medical invoice; halting execution of the step in which the application management component causes the sequence of the server applications to process the electronic medical invoice; and sending a processing error message to the sender application.

This embodiment can be advantageous because it can provide for optimal algorithm of processing of errors related to pattern recognition. The error in processing of one electronic medical invoice does not cause disruption in processing of other electronic medical invoices.

According to another embodiment of the present invention, the electronic medical invoice comprises a user identification information assigned to a user. The application management component is operable for configuring the server applications. The execution of the executable code by the processing unit cases the server to execute the following: the application management component configuring another receiver application of the set of the server applications to perform the following: receiving via a computer network from a sender application executed on an identity provider server user credentials assigned to a user to whom the electronic medical invoice is deemed to be assigned; converting the user credentials in a format parsable by a processing application of the sequence; and sending the converted user credentials to said processing application. The execution of the executable code by the processing unit cases the server to execute the following: the application management component configuring said processing application to perform the following when said processing application executes the processing of electronic medical invoices assigned to the user: receiving from the another receiver application the converted user credentials; and sending an error message to the application management component when the user identification information comprised in the electronic medical invoice and the received converted user credentials are not assigned to the same user.

This embodiment can be advantageous because it can provide for an extra control for correctness of processing of the electronic medical invoices. The extra functionality for controlling the correctness is activated in a way that it does not require substantial modification of the sequence of the server applications.

FIG. 1 illustrates an example environment for processing electronic medical invoices. Specifically, the illustrated environment includes an electronic payment system for reimbursement of medical costs. The electronic payment system comprises a server 140 comprising a database 130, hardware resources 128 comprising memory and a processing unit (e.g. at least one computer processor). The server 140 is operable for execution of applications 121, 122, 127, 124, 125, 126, 129 and an application management component 123. The server 140 is communicatively coupled to end terminals (e.g. end terminal 110) via computer networks (e.g. network 161). The network can be a digital cellular telecommunication network and the end terminal can be mobile phone, a handheld mobile telecommunication device (e.g. a tablet), a gadget operable for receiving electronic medial invoices and sending them to the server 140, etc. The server 140 can be communicatively coupled via computer network 163 to an identity provider server 150. The identity provider server is configured to provide user credentials to the server 140 when end terminals operated by users establish connection to the server 140. The user credentials are user credentials of users operating the end terminals. The server can verify whether an electronic medical invoice sent form an end terminal operated by a user corresponds to said user by comparing his credentials used for login to the server 140 and user identification information in the electronic medical invoice sent by said user. When the user credentials and the user identification correspond to the same user then the verification is successful and the received electronic medical invoice indeed corresponds/is assigned to said user. The identity provider server can be communicatively coupled to the end terminals via computer network 162. The computer network 162 can be a digital cellular telecommunication network. The end terminal can be configured to perform a procedure of identification of a user operating the end terminal on the identity provider server 150. If the identification of the user is completed successfully a sender application 151 executed on the identity provider server 150 sends a user credentials of the user to a respective receiver application executed on the 140, wherein the user credentials enable login of the user to the server 140 and subsequent sending of electronic medical invoices of the user and other related information to the server 140.

The application management component 123 is operable for constructing sequences of applications executed in the server for processing the electronic medical invoices and performing reimbursement of costs related to the received electronic medical invoices. The application management component is further operable for configuring of applications. The applications used in a sequence of applications can be configured by the application management component before starting operation of said sequence. In addition, the application management component can configure applications in a sequence of applications being in operation as well, i.e. executing processing of electronic medical invoices. The application management component is configured for monitoring and processing of information including received by the server electronic medical invoices, user credentials, and other related information. This information can be used for constructing new sequences of applications or modification of being in operation sequences of applications. The application management component is further operable for managing of internal and external data exchange, wherein internal data exchange comprises data exchange (e.g. electronic medical invoices) between the applications executed on the server 141 and the external data exchange comprises data exchange between pairs of sender and receiver applications, the application management component and applications executed on other electronic devices (e.g. the end terminals, the identity provider server, the health insurance provider server).

The applications executed on the server 140 comprise receiver applications, 122, 121, 127, processing applications 124-126, and a health insurance provider application 129. Alternatively the health insurance provider application can be executed on a server of a health insurance provider. In this case the health insurance provider server is communicatively coupled with the server 140. The receiver application is an application configurable for receiving electronic medical invoices and/or information related to processing of electronic medical invoices. The electronic medical invoices and/or the information related to processing of the electronic medical invoices can be received from respective sender applications 111, 112 executed on the end terminals (e.g. end terminal 110) and/or respective sender applications (e.g. sender application 151) executed on the identity provider server 150. Pairs of sender and receiver applications (e.g. 111 and 121, 112 and 122, 151 and 127) can be configured for communicating from the end terminal (e.g. 110) or the identity provider server (e.g. 150) to the server 140 information of specific type. For instance one pair of sender receiver applications (e.g. 111 and 121) can be configured for sending electronical medical invoices from the end terminal (e.g. 110) to the server 140 via a specific computer network (e.g. 161). The electronic medical invoices sent via this communication channel can be electronic medical invoices of a specific type. The type of the electronic medical invoice can be determined by one or more of the following features of the electronic medical invoice: the electronic medical invoice is a medical invoice of a particular health care provider, the electronic medical invoice is addressed to a particular health insurance provider (e.g. a particular insurance company), the electronic medical invoice is addressed to a particular user (e.g. a particular physical person), the electronic medical invoice is formulated in a particular format, the electronic medical invoice is assigned to a particular user or a group of users etc. The formats in which the electronic medical invoices can be formulated can be but are not limited to: an electronic message format (e.g. E-Mails), an electronic document format (e.g. pfd format, text format, Microsoft office document format, etc.), a digital image (e.g. a digital image of a medical invoice printed on a carrier).

The processing application is an application configurable for execution of a specific operation related to processing of the electronic medical invoices and/or reimbursement of costs related to the electronic medical invoices. Such an operation can be for instance extracting data in text format from an image comprised of an electronic medical invoice. Another operation can be processing of the electronic medical invoices assigned to a user or a group of users according to a user specific rule. For instance a user specific rule can specify that only a certain percentage of costs specified in electronic medical invoices of a user or a group of users are to be reimbursed. Thus processing of an electronic medical invoice according to this rule means that costs specified in the electronic medical invoice have to be corrected by a factor specified in a user specific rule. Another user specific rule for processing electronic medical invoices can be a user specific rule determining processing of electronic medical invoices of a user or a group of users in conjunction with a user specific information. For instance, the user specific information can be information related to his compliance with his health care plan. The health care plan can be provided by a health care provider of the user (e.g. by a doctor treating the user). An example of such a rule can be a rule determining a percentage of medical costs specified in electronic medical invoices of a user in dependence of a number of visits of the user to a health care facility, e.g. fitness clubs. For instance, when the user visits the fitness facility more than a predetermined number of times, his medical costs are fully reimbursed, otherwise only a predetermined percentage of his costs is reimbursed. Thus an application configured to process the medical electronic invoices according to the user specific rule receives costs extracted from the electronic medical invoice of the user and a number of his visits to the fitness facility. When the number is bigger than a predefined threshold value it forwards the costs to another processing application without correction, otherwise it corrects the costs by a factor specified in the user specific rule.

The user specific information required for processing of medical costs according to user specific rules can be received from dedicated applications on end terminals of users. These dedicated applications can collect the user specific information from health care devices 113 and/or health monitoring devices 114. A health monitoring device can be for instance a blood pressure measurement device, a heart rhythm measurement device, etc. A health care device can be for instance a fitness device, a massage device, a device for administration of medications, etc. These dedicated applications can establish connections to said devices via various connections such as Bluetooth, Wi-Fi, and other computer networks. Users concerned about their privacy, i.e. users who do not want to send the aforementioned user specific information, can deactivate the applications on their end terminals which are configured to collect the user specific information. In this case, the processing applications configured to process electronic medical invoices according to user specific rules in conjunction with the user specific information can be configured to process the electronic medical invoices using default options of the user specific rules determining processing of the electronic medical invoices when no user specific information is provided. The processing application can be configurable not only to process electronic medical invoices assigned to a user in conjunction with user specific information of the user according to a user specific rule but to cause an end terminal of the user to collect the user specific information from the one or more health care devices and/or the one or more health monitoring devices. In order to preform this, the processing application can send a specification of the user specific information which is needed for processing of the electronic medical invoices of the user according to the user specific rule. The processing application can perform the causing of the end terminal to collect the user specific information via respective pair of the sender and the receiver application which are configured to send the user specific information from the end terminal to the server.

The application management component can be further operable for monitoring workload of the applications executed on the server 140. It can be further operable for assigning hardware resources of the server 140 to the applications executed thereon. The management of the workload of the applications can be performed by monitoring of a number of electronic medical invoices to be processed by the application executed on the server. The management of the workload can further comprise storing sets of electronic medical invoices to be processed by one of the electronic medical invoices in the database 130. In the other words, database 130 can function as a workload buffer for electronic medical invoices to be processed by the applications executed on the server 140. In addition the database can store user specific rules determining processing of the electronic medical invoices assigned to particular users.

The health insurance provider application 129 can be operable for monitoring information related to reimbursement of medical costs according to electronic medical invoices received by the server 140. The information related to reimbursement of medical costs can comprise actual amount to be reimbursed to a user in accordance with a respective electronic medical invoice received by a respective receiver application executed on the server 140. The information related to reimbursement of the medical costs can be sent to a health insurance provider, e.g. an insurance company with which the user has a heath care contract (e.g. insurance). The application of the health insurance provider can be further operable for generating and/or updating of the user specific rules on a basis of the information for the reimbursement of the medical costs. For instance, when a user has an overall amount of medical costs to be reimbursed in a predefined interval of time below a predefined threshold value, then the application of the health care application can modify a user specific rule determining percentage of medical costs to be reimbursed to the user, e.g. increase the percentage to be reimbursed.

Figure 2:
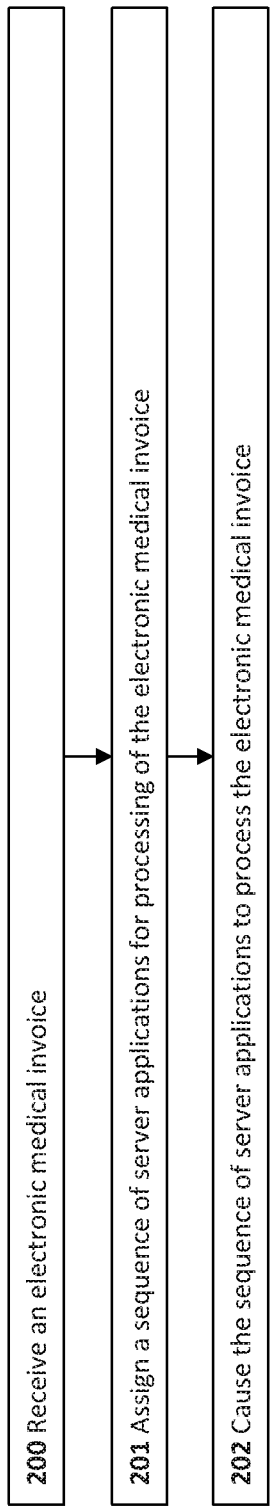
FIG. 2 shows a flowchart of an example method for processing of the electronic medical invoices.

The memory of the server can store a computer executable code, which when executed by the processing unit cases the server to execute a method which flow chart is depicted on FIG. 2. The method begins with process block 200. In process block the server 140 receives via a digital cellular telecommunication network 161 an electronic medical invoice from a sender application 111 executed on an end terminal 110. Each electronic medical invoice received in process block 200 can be assigned to a respective user. Further each of some or all electronic medical invoices received in process block 200 can comprise user identification information of the user to whom the received medical invoice is assigned. The user identification information can comprise at least one of the following his name, his identification number, his address, his date of birth.

Process block 201 is executed after process block 200. In process block 201 the application management component 123 assigning a sequence of the server applications (e.g. 121, 124, 125, 126) of the set of server applications for processing of electronic medical invoices. The assignment of the sequence of the server applications can comprise configuration of at least one of the server applications by the application management component 123. An application being the first in the sequence (e.g. 121) is a receiver application configured to receive and to process the electronic medical invoice. For instance this receiver application can be configured to establish a secure computer network connection with said sender application executed on the end terminal. This connection can be optimized for receiving of electronic medical invoices of the same type. The receiver application can be further configured to receive electronic medical invoices (of the same type as option) from other sender applications executed on other end terminals. Each next server application in the sequence is configured to process further the electronic medical invoice previously processed by the server application being in the sequence immediately before the each next server application in the sequence. The last server application in the sequence (e.g. 126) is configured to execute reimbursement of medical costs according to the electronic medical invoice processed by the server applications of the sequence of the applications. In the other words, the server applications of the sequence are configured to perform pipeline processing of the received electronic medical invoices. Each server application in the sequence can be configured to execute a specific operation on the received electronic medical invoice. The execution of the reimbursement of the medical costs can be executed by sending a payment order to a bank institution. The execution of the reimbursement of the medical costs can comprise sending an information for the reimbursement of the medical costs to a health insurance provider. For instance, the information can be sent to an application 129 of the health insurance provider. The application 129 can be configured to check the correctness of the information for the reimbursement. When the information for the reimbursement is not correct, the application 129 can prevent execution of the payment order by the bank institution.

The functioning of the aforementioned sequence of the server applications can be illustrated on the following example in greater detail. The processing application 124 is configured to receive the electronic medical invoice received and processed by the receiver application 121, to process the electronic medical invoice received from the receiver application 121, and to send the electronic medical invoice processed by the processing application 124 to the processing application 125 being the next in the sequence. In its own turn, the processing application 125 is configured to receive the electronic medical invoice processed by the processing application 124, to process the electronic medical invoice received from the receiver application 124, and to send the electronic medical invoice processed by the processing application 125 to the processing application 126 being the next in the sequence. Finally, the processing application 126 is configured to receive the electronic medical invoice processed by the processing application 125, to process the electronic medical invoice received from the receiver application 125, and to execute reimbursement of medical costs according to the received electronic medical invoice processed by the server applications of the sequence 121, 124, 125, 126.

As it is mentioned before, each server application in the sequence can be configured to execute a specific operation on the received electronic medical invoice. In this example the receiver application 121 is configured to receive the electronic medical invoices. The receiver application 121 being the first in the sequence can be configured to receive only electronic medical invoices of a specific type, i.e. electronic medical invoices being electronic files comprising images of medical invoices printed on a carrier (e.g. paper). The processing application 124 being the second in the sequence is configured to extract text data from image of the text data comprised in the image of the medical invoice. The text data can comprise company details of a medical institution which has issued the medical invoice (e.g. address of the medical institution, its contact details, etc.), medical costs and their specifications, user identification formation (e.g. name of patient who has received medical treatments which costs are specified in the medical invoice, his date of birth, etc.). The text data extracted from the image of the medical invoice by the processing application is sent by it to the processing application 125 being the third server application in the sequence. The processing application 125 can be configured to determine a percentage of medical costs to be reimbursed on a basis of information comprised in the data received from the processing application 124 in accordance with a user specific rule specified for the user which identification information is comprised in the electronic medical invoice. The processing application 125 can be configured to append the determined percentage to the data received from the processing application 124 and to send the aggregate data to the processing application 126 being the fourth in the sequence. In case when there is no user specific rule, the processing application 125 can be configured to forward data received from the processing application 124 to the processing application 126 without changes. The processing application 126 can be configured to generate an instruction to a financial institution to reimburse the medical costs (or a percentage of them if applicable) as specified in data received from the processing application 125.

Turning back to flow chart depicted on FIG. 2. Process block 202 is executed after process block 201. In process block 202 the application management component causes the sequence of the server applications to process the electronic medical invoice. The application management component can cause the sequence of the server application to process further electronic medical invoices received by the server.

As it is mentioned above each electronic medical invoice can have a respective type. For instance, electronic medical invoices of one type can be electronic medical invoices having a text format, while electronic medical invoices of another type comprise images of medical invoices printed on carriers. The application management component can be configured to assign a respective customized sequence of the server applications of the set of the server applications for processing of each of the types. The aforementioned in process block 201 sequence can be one of the customized sequences of the server applications. At least two of the customized sequences of the server applications can have common fragments of the sequences of the server applications (i.e. use common server applications). Each of the customized sequences of the server applications begins with a respective receiver application for receiving and processing of the electronic medical invoices of the type for which the each of the customized sequences of the server applications is customized. For instance, the aforementioned sequence of server applications 121, 124, 125, 126 can be one of the customized sequences. Another customized sequence can be a sequence of the server applications 127 and 126. The processing application 126 is used by both of the customized sequences. The receiver application 127 being the first in the sequence can be configured to receive electronic medical invoices in text format. The electronic medical invoices of this type can be received from sender applications executed on the end terminals via computer networks. A secure computer network communication protocol can be used if necessary. Since the electronic medical invoices of this type are already in text format, there is no need to use the processing application 124 as in the example related to sequence of server applications 121, 124-126. In addition, no user specific rules are used for reimbursement of medical costs specified in the electronic medical invoices received via the receiver application 127. The processing application 126 being the second in this sequence is configured to process the electronic medical invoices which are received from the receiver application 127. The processing application 126 processes the electronic medical invoices received from the receiver application 127 in the sequence of the server applications 127 and 126 in the same way as the electronic medical invoices received from the processing application 125 in the sequence of the server applications 121, 124-126.

Process blocks 200-202 can be repeated for further electronic medical invoice received in process block 200. Process blocks 200-202 can be executed in parallel for different medical electronic invoices.

As it is mentioned above, the application management component can be operable for monitoring a number of electronic medical invoices to be processed by the server applications, wherein the (customized) sequences of applications can comprise one or more of these server applications for which the respective numbers of the electronic medical invoices to be processed by any of them can be registered. Moreover some of these server applications are configured to process the electronic medical invoices in two modes. In one mode of the two modes (i.e. first mode) the electronic medical invoices are processed one by one, while in another one of the two modes (i. e. second mode) the electronic medical invoices of the same type are processed batch wise. The execution of the executable code by the processing unit cases the server to execute the following: the application management component causing the server application to process the electronic medical invoices in the second mode when a number of the electronic medical invoices of the same type to be processed by said server application is bigger than a predefined first number otherwise the application management component causing said server application to process the electronic medical invoices in the first mode. The performance of this feature can be readily understood on a basis of the following example, wherein electronic medical invoices of one type are electronic medical invoices to be reimbursed by one health insurance provider and electronic medical invoices of another type are electronic medical invoices to be reimbursed by another health insurance provider. Processing of the electronic medical invoices of one type batch wise when a number of them to be processed by the server application is bigger than a predefined value can reduce time for searching user specific rules for processing of them by said server application, because the health insurance provider can have the same user specific rules for all or groups of users.

As it is mentioned above the application management component can be operable for monitoring a work load of the server application of the sequence of the server applications. In addition the application management component can be operable for allocating hardware resources of the server for execution of the server applications. The execution of the executable code by the processing unit cases the server to execute the following: the application management component allocating respective hardware resources of the server for execution of each of the server applications of the sequence of the server applications in conjunction with the respective work load of the each of the server application of the sequence of the server applications such that time required for processing of electronic medical invoices by the sequence of the server applications. Implementation of this feature can be straight forward, because the server applications are configured to execute their respective specific operations. This in conjunction with the assignment of each medical invoice received by the server to a respective customized server application for processing enables forecasting a number of operations to be executed by each of the server applications versus time. In the other words, this approach enables simple calculation of time dependence of the work load of each of the server applications comprised in the sequence (or the sequences). When the workload of the server application is known it is easy to determine hardware resources required for processing of the workload according to the calculated time dependence of the workload, because of customization of the server application for execution of a specific operation, i.e. because time needed for processing of a number of the electronic medical invoices by the server application is proportional to said number when hardware resources allocated for processing of said number of the electronic medical invoices is fixed.

In general the aforementioned problem of the effective allocation of hardware resources for minimization of time needed for processing of the electronic medical invoices can be formulated as a problem a minimization of a mathematical functional determining time required to process the set of electronic medical invoices in conjunction with hardware resources allocated for execution of each of the server applications used for processing of the electronic medical invoices of the set, wherein hardware resources allocated for execution of the each of the server applications determine time needed for processing of the electronic medical invoices to be processed by the each of the server applications.

Figure 3:
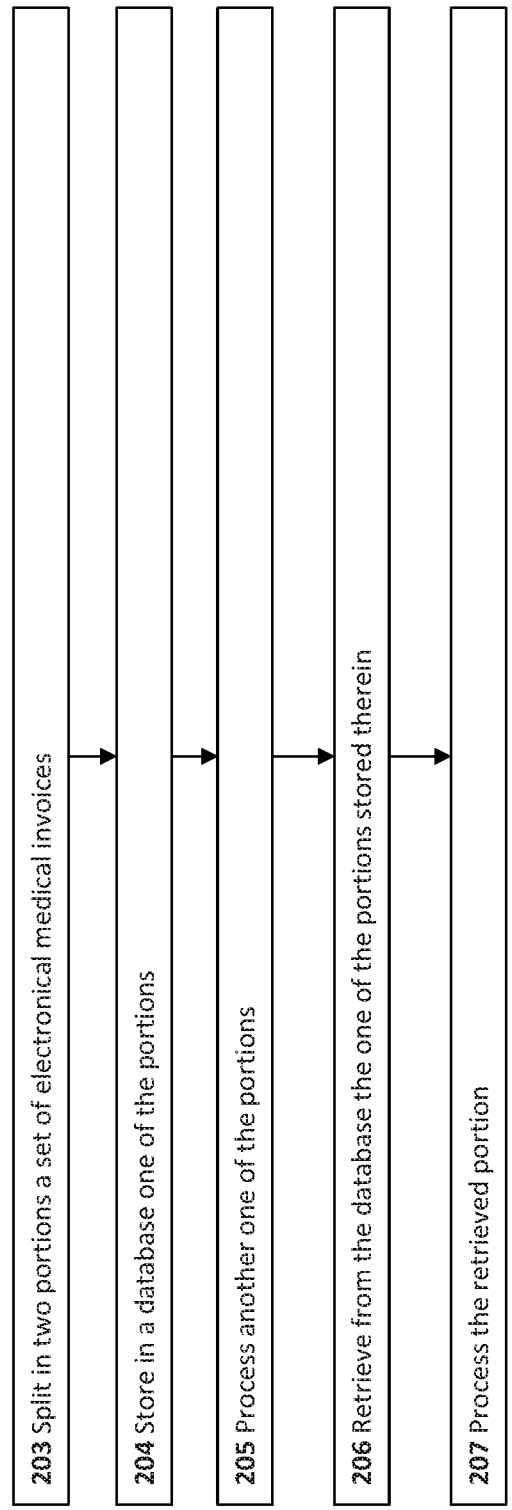
FIG. 3 shows a flowchart of an example method for processing of the electronic medical invoices.

The memory of the server can store a computer executable code, which when executed by the processing unit cases the server to execute a method which flow chart is depicted on FIG. 3. The method depicted on FIG. 3 is used for harmonization of the workload of the electronic medical invoices to be processed by the server application. The aforementioned approach for allocation of the hardware resources for processing of the electronic medical invoices can function without reconsidering of allocation of the hardware resources when the flux of the electronic medical invoices can be accurately predicted, which is possible for some applications, and when processing of the electronic medical resources has high priory among other processes execute on the server, i.e. when the demand for hardware resources needed for execution of the server applications processing the electronic medical invoices is satisfied first in comparison with other demands for allocation of hardware resources. The latter may be not always the case, because other processes like maintenance of the server can have higher priorities than the processing of electronic medical invoices on the server.

The method depicted on FIG. 3 begins with process block 203. In process block 203 a server application splits in two portions a set of electronic medical invoices (i.e. in a first portion of electronic medical invoices and second portion of electronic medical invoices) to be processed by said server application when a number of the electronic medical invoices of the set exceeds a second predefined number. When the latter is the case further process blocks 204-207 are executed. Process block 204 is executed after process block 203 when the application management component has split in two portions said set. In process block 204 the server application stores in the database 130 one of the two portions (i.e. the first portion). Process block 205 is executed after process block 204. In process block 205 the server application processes another portion (i.e. the second portion) of the two portions. Process block 206 is executed after process block 205. In process block 206 the server application retrieves from the database 130 the one (i.e. the first portion) of the two portions. Process block 207 is executed after process block 206. In process block 207 the server application processes the one portion (i.e. the first portion) of the two portions retrieved from the database after the another one (i.e. the second portion) of the two portions is processed by said server application.

The server application executing method depicted on FIG. 3 can be the server application of the sequence of the server applications assigned for processing of electronic medical invoices in process block 201. The method depicted on FIG. 3 can be executed by the application management component. In this case the application management component causes said server application to execute the method. Said server application can comprise another database which can be used for execution of the method depicted on FIG. 3 instead the database of the server.

Figure 4:
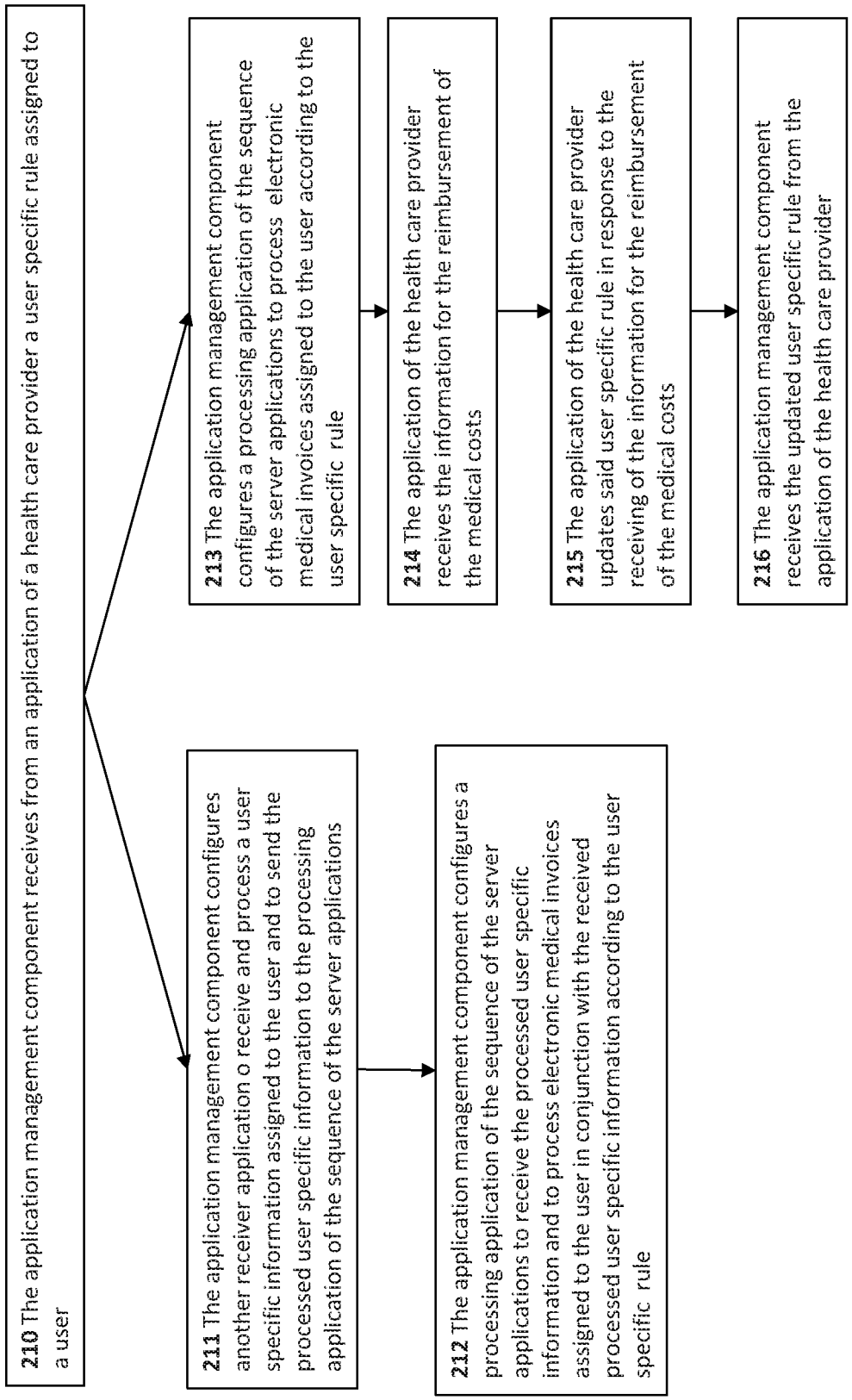
FIG. 4 shows a flowchart of an example method for processing of the electronic medical invoices.

The memory of the server can store a computer executable code, which when executed by the processing unit cases the server to execute a method which flow chart is depicted on FIG. 4. The method depicted on FIG. 4 begins with process block 210. In process block 210 the application management component receives from the application 129 of the health insurance provider a user specific rule assigned to a user. Process block 213 is executed after process block 210. In process block 213 the application management component configures the processing application (e.g. 125) of the sequence of the server applications (e.g. 121, 124-126) to process the electronic medical invoices assigned to said user according to the received user specific rule. Process block 213 can be executed before or after execution of process block 202. When process block 213 is executed before execution of process block 202 and the electronic medical invoice received therein is assigned to said user then the electronic medical invoice received in process block 200 is processed by the processing application in process block 202 according to the user specific rule, otherwise a next electronic medical invoice assigned to said user and received in a course of repetitive execution of process block 200 is processed by the processing application in a course of repetitive execution of process block 202 according to the user specific rule.

Optional process blocks 214-216 can be executed after process block 213. Optional process block 214 is executed after process block 213. Its execution is triggered by execution of process block 202, wherein the execution of the reimbursement of medical costs according to the electronic medical invoice processed by the server applications of the sequence of the server applications comprises sending information for the reimbursement of the medical costs to the application of the health insurance provider. The information for the reimbursement of the medical costs is generated in accordance with the electronic medical invoice received in process block 200. In process block 214, the application of the health insurance provider receives the information for the reimbursement of the medical costs. The information for the reimbursement of the medical costs is sent by the processing application of the sequence. Process block 215 is executed after process block 214. In process block 215 the application of the health insurance provider updates said user specific rule on the basis of the information for the reimbursement of the medical costs in response to the receiving of the information for the reimbursement of the medical costs. Process block 216 is executed after process block 215. In process block 216 the application management component receives the updated user specific rule from the application of the health insurance provider. Afterwards execution of process block 213 can be repeated. As a result thereof the processing application in the sequence will process according to the updated user specific rule a next electronic medical invoice assigned to said user in a course of a repetitive execution of process block 202 when the next electronic medical invoice is received in a course of a repetitive execution of process block 200.

Another version of the user specific rule can be received in process block 210. The user specific rule can determines processing of his electronic medical invoice in conjunction with his user specific information being descriptive of his compliance with his health care plan provided by his health care provider. As it is mentioned above the user specific information can comprise a number of times the user has visited a health care facility. When this user specific rule is received in process block 210, process block 211 is executed after process block 210 instead of process block 213. In process block 211 the application management component configures another receiver application (e.g. 122) of the set of the server applications to perform the following: (a) receiving the user specific information via a computer network 161 (e.g. the digital cellular telecommunication network) from another sender application 112 executed on the end terminal 110; (b) converting the received user specific information in a data format being parsable by a processing application (e.g. 125) of the sequence (e.g. 121, 124-126) of the server applications; and (c) sending the converted user specific information to said processing application. The receiving of the user specific information can be performed using a secure computer network protocol. The step (b) is used because process block 211 can be executed independent of process block 201, or even after process block 202, when the sequence of server applications is already operating. When the any of the latter options is the case, preparation of the data in a suitable format can minimize reconfiguration of the sequence of the server applications is already in operation or is prepared for operation.

Process block 212 is executed after process block 210 or process block 211. In process block 212 the application management component configuring the processing application to which the another receiver application is configured to send the converted user specific information, to perform the following: (d) receiving from the another receiver application the converted user specific information; (e) and executing the processing of electronic medical invoices assigned to the user in conjunction with the received converted user specific information according to the user specific rule. Execution of process steps (a)-(e) becomes mandatory in a course of execution or repetitive execution of process block 202 after execution of process blocks 211 and 212 and receiving an electronic medical invoice assigned to said user in process block 200. Optional process blocks 214-216 can be executed after process block 212 in the same way as after they are executed after process block 216.

The method depicted on FIG. 4 can comprise yet another optional process block, wherein the application management component causes the processing application configured in process block 212 to cause the end terminal via the another sender application 112 executed on the end terminal 110 of said user and the another receiver application 122 configured in process block 211 to collect the user specific information from the one or more health care devices and/or the one or more health monitoring devices. This way of obtaining the user specific information can be effective because it relies on already configured communication channel between the server 140 and the end terminal 110.

The electronic medical invoice can be an electronic file comprising a digital image of a medical invoice printed on a substrate (e.g. paper). The image is a mixed digital text/graphic image comprising text data and graphical objects. The text data comprise at least one of the following: company details of a health care provider which has issued the medical invoice (e.g. address and contact details of a hospital or a general practitioner), specification of medical treatments and their costs, logotype of the health care provider which has issued the medical invoice. The reimbursement of the medical costs can be executed on a basis of the extracted costs and specification of the medical treatments. The graphical objects comprise logotype of the health care provider. The digital image of the medical invoice can be made by a photo camera of a mobile phone.

One of the server applications in the sequence of the server applications can be configured to extract text data from the images of medical invoices. Extracting of text data from digital images is performed using pattern recognition methods. More than one method can be used for extracting of the text data because the digital image is a mixed text/graphic image comprising images of text data (e.g. company details, specification of medical treatments, costs) and at least one graphical object (e.g. logotype of the health care provider). One method can be customized for identifying graphical objects in the digital image and another method can be customized for extracting text data from the images of text data.

The step in process block 202 in which the application management component causes the sequence of the server applications to process the electronic medical invoice can comprise the following: one of the server applications in the sequence extracting text data from the image of the medical invoice comprised in the electronic medical invoice. Wherein the step in which the one of the server application extracts the text data form the image comprises the following: identifying one or more graphical objects in the image using a first pattern recognition method; generating an auxiliary image by subtracting image of the one or more graphical objects from the image; and identifying the text data in the auxiliary image using a second pattern recognition method. The subtracting of the image of the one or more graphical objects from the image can be performed on a pixel basis, wherein a pixel value (e.g. intensity) of the image of the one or more graphical objects is subtracted from the respective pixel value of the image. Alternatively, the subtracting of the image of the one or more graphical objects image from the image can be assigning one or more areas in the image to the image of the one or more graphical objects and the rest of image area to the auxiliary image.

The first pattern recognition method can comprise the following steps: a first step being in an optional one is a preprocessing of the image (applying different filters to an image, correction of its orientation, correction of its contrast, etc.), a second set is a feature extraction from the image, a third step is classification of the features and identification of graphical objects in the image on a basis of the classification of the features. The feature extraction can be executed using a set of wavelet functions. The set of wavelet functions can be for instance a set of Gabor wavelet functions, or a set of Haar wavelet functions, or a set of Meyer wavelet dunctions. The correctness of the graphical objects identified using the first pattern recognition can be checked by comparing of the identified graphical objects with graphical objects stored in the database 130. When none of the identified graphical objects matches is stored in the database then it can be an indicative of failure of the first pattern recognition method. This feature can improve reliability of processing of the images because graphical objects can be logotypes of the health care providers which can be stored in the database 130 upfront. It is customary in the health care sector, that all health care providers are licensed and registered. Thus their logotypes and company details can be obtained from government/dedicated databases.

Since the spectrum of the graphical images to be identified in the electronic medical invoices can be very broad, just because the diversity of the logotypes is only limited by fantasy and wishes of the health care providers, different sets of wavelet functions can be used for feature extraction method comprised in the first pattern recognition method. When execution of the first pattern recognition method did not result in identification of a graphical object stored in the database, it can be repeated using another set of wavelet functions used for the feature extraction method. The database 130 can store different sets of wavelet functions which can be tried one by one until the first pattern recognition method identifies one of the graphical objects stored in the database.

The second pattern recognition method can be a statistical pattern recognition method or any other method for converting images of text data in data in text format. Its performance is supported by execution of the first pattern recognition method. The second pattern recognition method processes the auxiliary image, in which the graphical objects identified by the first pattern recognition method are removed. Thus this image processed by the second pattern recognition method is much more homogeneous in comparison with the original image of the medical invoice. In addition, using the successfully identified logotype of the health care provider by the first pattern recognition method it is possible to use reference character set customized for said health care provider in the second pattern recognition method. The database can store reference character sets, wherein each of the reference character sets is associated with the respective graphical image for identification by the first pattern recognition method. Another useful feature which can be implemented when two pattern recognition methods process the image of medical invoice one by one is checking correctness of text data identified by the second pattern recognition method. The database can store company details of health care providers as in text format. Each text related to the company details of the health care provider can be associated in the database with a respective graphical image for identification by the first pattern recognition method. When the second pattern recognition method identifies no text data in the image which according to the data base has to be company details of the health care provider which logotype was previously identified in the image by the first pattern recognition method, then it can indicate that the second pattern recognition method did not work correctly. In can also indicate that execution of the first pattern recognition method re-suited in identification of a wrong logotype. When utilization of different wavelets did not result in identification in the image of the logotype and company details being according to the database associated with each other, then the processing application executing these methods can send an error message to the application management component. In response to receiving the error message from the processing application the application management component can forward to the health insurance provider application the electronic medical invoice comprising said image to the health insurance provider application marked as machine unparsable. In addition or as alternative the application management component can send a processing error message to the end terminal from which said electronic medical invoice was received, wherein the processing error message indicates that said electronic medical invoice cannot be processed automatically. Yet another alternative or additional step is a step in which the application management component halts execution of process block 202 related to processing the electronic medical invoice comprising said image and/or aborts the execution of the step of the one of the server applications in the sequence extracting text data from the image of the medical invoice comprised in the electronic medical invoice.

Figure 5:
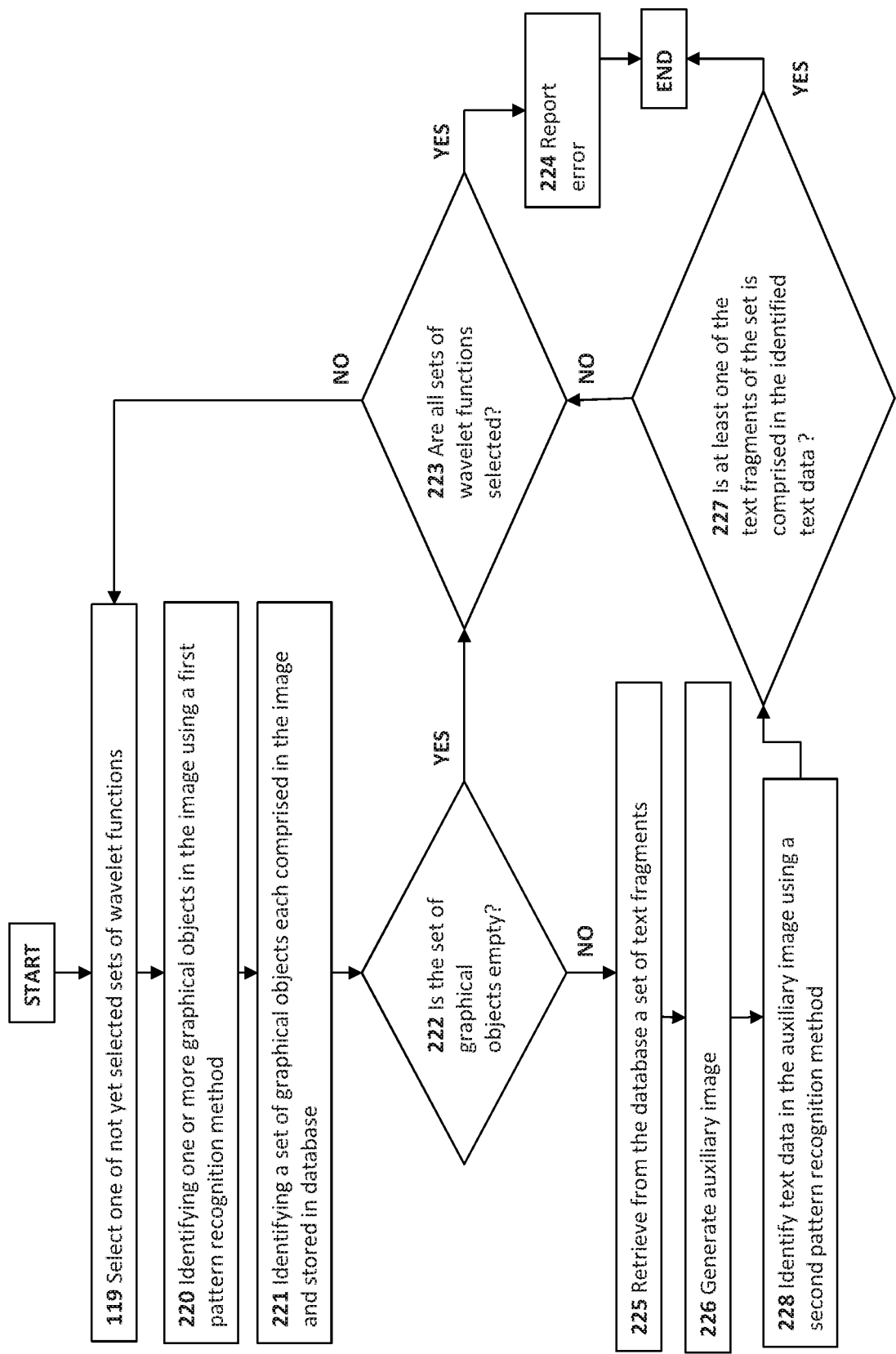
FIG. 5 shows a flowchart of an example method for processing of the electronic medical invoices.

FIG. 5 depicts a flow chart diagram of an extended method based on the aforementioned principles. The verification of correctness of extracting the text data from the digital image of the medical invoice is checked using a database storing graphical images and text fragments, wherein each graphical image is associated with the respective text fragment. When the graphical object identified by the first pattern recognition method and the text fragment identified by the second pattern recognition method are stored in the database and associated with each other then processing of the image is considered to be correct and the text data identified by the second pattern recognition method is outputted as a result of extracting of the text data by the processing application using these two methods.

The method depicted on FIG. 5 begins with process block 199. In process block 199 one of the not yet selected sets of the wavelet functions stored in the database is selected for execution the feature extraction method comprised in the first pattern recognition method. Process block 220 is executed after process block 220. In process block 220 one or more graphical objects are identified in the image using a first pattern recognition method, wherein the feature extraction of the features of the one or more graphical objects is performed using the selected set of wavelet functions. Process block 221 is executed after process block 220. In process block 221 a set of graphical objects is identified. Each of the graphical objects of the set of graphical objects is stored in the database and identified in the last execution of process block 220. Decision process block 222 is executed after process block 221. Decision process block causes execution of process decision process block 223 when the set of graphical images identified in the last execution of process block 221 is empty, otherwise decision process block causes execution of process block 225.

Decision process block 223 causes execution of process block 119 when database stores at least one not yet selected in previous execution of process block 119, otherwise decision process block 223 causes execution of process block 224. In process block 224 the processing application executing this method sends an error message to the application management component. After execution of process block 224 the execution of the method is completed.

In process block 225 a set of text fragments of text fragments is retrieved from the database. Each of the text fragments of the set of text fragments is associated with the respective graphical object of the set of graphical objects identified in the last execution of process block 221. Process block 226 is executed after decision process block 222 or after process block 225. In process block 226 an auxiliary image is generated by subtracting from the image an image of the one or more graphical objects identified in the last execution of process block 220. Process block 228 is executed when execution of process blocks 225 and 226 is completed. In process block 228 text data in the auxiliary image which is generated in the last execution of process block 226 is identified using a second pattern recognition. Decision process block 227 is executed after process block 228. Decision process block 227 causes execution decision process block 223 when none of the text fragments of the set of text fragments retrieved from the data base in the last execution of process block 225 is comprised in the text data identified in the last execution of process block 228 otherwise the method is completed and the text data identified in the last execution of process block 228 is the text data retrieved from the image of the medical invoice by the processing application executing the method depicted on FIG. 5.

In response to receiving the error message sent in process block 224 the application manager executes the following: aborting execution of the step in which the one of the server application extracts text data form the image comprised in the electronic medical invoice (this step comprises execution of the method depicted on FIG. 5); halting execution of the step in which the application management component causes the sequence of the server applications to process the electronic medical invoice (process block 202); and sending a processing error message to the sender application from which the electronic medical invoice comprising said image is received.

As it is mentioned above, each electronic medical invoice can be assigned to a respective user. The electronic medical invoice assigned to the user comprises a user identification information assigned to him. The user identification information can be at least one of the following: a user name, a user birthday, a user address, a user identification number. In the other words the user identification information functions as his unique identification. The assignment of the electronic medical invoice to a particular user can be verified as follows. The user credentials are sent to the server when a connection is established between the server and the end terminal operated by a user having said user credentials. The user credentials can be for instance sent to the server by the identity provider server. After the user credentials received by the server the electronic medical invoices received from the end terminal operated by the user are deemed to be assigned to him. The verification of assignment is performed by comparing assignment of the user credentials received by the server with assignment of the user identification info comprised in the electronic medical invoice. When the user credentials and the user identification are not assigned to the same person then there is a failure. Such a failure can occur, when the user sends to the server via his end terminal by mistake an electronic medical invoice addressed to another person.

The aforementioned approach for verification of the assignment can be implemented as follows. The execution of the executable code by the processing unit cases the server 140 to execute the following: the application management component 123 configuring another receiver application (e.g. 122) of the set of the server applications to perform the following: receiving via a computer network 162 from a sender application (151) executed on the identity provider server (151) user credentials assigned to a user to whom the electronic medical invoice is deemed to be assigned; converting the user credentials in a format parsable by a processing application (e.g. 125) of the sequence (e.g. 121, 124-126); and sending the converted user credentials to said processing applications. The execution of the executable code by the processing unit cases the server 140 to execute further the following: the application management component configuring said processing application (e.g. 125) to perform the following when said processing application executes the processing of electronic medical invoices assigned to the user (e.g. in process block 202): receiving from the another receiver application the converted user credentials; and sending an error message to the application management component when the user identification information comprised in the electronic medical invoice and the received converted user credentials are not assigned to the same user.

When an electronic medical invoice deemed to be assigned to a user is received by the server from an a sender application executed on an end terminal operated by said user (e.g. process block 200) its assignment verification is executed as follows using the receiver and processing applications configured as described above. Since the electronic medical invoice is received by the server user credentials of the user to whom the received electronic medical invoice is deemed to be assigned are already received by said configured receiver application. After the receipt of the electronic medical invoice the application management component assigns a sequence of server applications for processing of the received electronic medical invoice (e.g. process block 201), wherein the assigned sequence comprises said configured processing application. As a next step the application management component causes the sequence of server applications to process the received electronic medical invoice (e.g. process block 202), wherein in a course of processing of the received medical invoice by the sequence of server applications said configured processing application receives from said configured receiver applications the converted user credentials and from preceding in the sequence server application the electronic medical invoice. Afterwards said configured processing application sends an error message to the application management component when the user identification information comprised in the electronic medical invoice and the converted user credentials are not assigned to the same user.

In response to receiving the error message the application manager executes the following: halting execution of the step in which the application management component causes the sequence of the server applications to process the electronic medical invoice (process block 202); and/or sending a processing error message to the sender application from which the electronic medical invoice is received.

The preceding figures and accompanying description illustrate the example processes and computer implementable techniques. But example environment (or their software or other components) contemplate using, implementing, or executing any suitable technique for performing these and other tasks. It will be understood that these processes are for illustration purposes only and that the described or similar techniques may be performed at any appropriate time, including concurrently, individually, in parallel, and/or in combination. In addition, many of the operations in these processes may take place simultaneously, concurrently, in parallel, and/or in different orders than as shown. Moreover, the example environment may use processes with additional, fewer and/or different operations, as long as the methods remain appropriate.

In other words, although this disclosure has been described in terms of certain implementations and generally associated methods, alterations and permutations of these implementations and methods will be apparent to those skilled in the art. Accordingly, the above description of example implementations does not define or constrain this disclosure. Other changes, substitutions, and alterations are also possible without departing from the spirit and scope of this disclosure.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example, a programmable processor, a computer, or multiple processors or computers. The apparatus can also be or further include special purpose logic circuitry, e.g., a central processing unit (CPU), a FPGA (field programmable gate array), or an ASIC (application specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, IOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, a FPGA, or an ASIC.

Computers suitable for the execution of a computer program can be based on general or special purpose microprocessors, both, or any other kind of CPU. Generally, a CPU will receive instructions and data from a read only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a global positioning system (GPS) receiver, or a portable storage device, e.g., a universal serial bus (USB) flash drive, to name just a few.

Computer readable media (transitory or non-transitory, as appropriate) suitable for storing computer program instructions and data include all forms of non-volatile memory, media and memory devices, including by way of example semiconductor memory devices, e.g., erasable programmable read-only memory (EPROM), electrically-erasable programmable read-only memory (EEPROM), and flash memory devices; magnetic disks, e.g., internal hard disks or removable disks; magneto optical disks; and CD ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), LED (Light Emitting Diode), or plasma monitor, for displaying information to the user and a keyboard and a pointing device, e.g., a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back end component, e.g., as a data server, or that includes a middleware component, e.g., an application server, or that includes a front-end component, e.g., a client computer having a graphical user interface or a web browser through which a user can interact with an implementation of the subject matter described in this specification, or any combination of one or more such back end, middleware, or front end components. The components of the system can be interconnected by any form or medium of wireline and/or wireless digital data communication, e.g., a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations. The network may communicate with, for example, Internet Protocol (IP) packets, Frame Relay frames, Asynchronous Transfer Mode (ATM) cells, voice, video, data, and/or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and/or software, may interface with each other and/or the interface using an application programming interface (API) and/or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API and/or service layer may be an integral and/or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any implementation or on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation and/or integration of various system modules and components in the implementations described above should not be understood as requiring such separation and/or integration in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

The invention claimed is:

1. An electronic payment system for reimbursement of medical costs, the system comprising:
   a server including a set of server applications including receiver applications and processing applications; and
   logic circuitry that is configured to,
   receive via a digital cellular telecommunication network an electronic medical invoice assigned to a user from a sender application executed on an end terminal of the user, wherein the electronic medical invoice includes an image including mixed text and graphics,
   cause the end terminal of the user to collect user specific information from one or more health care devices that provide health care to the user and/or one or more health monitoring devices that monitor the user, based on a specification of the user specific information according to one or more user specific rules for processing the electronic medical invoice, assign a sequence of the server applications of the set of server applications for the processing of the electronic medical invoice, wherein an application being first in the sequence is a receiver application configured to receive and to process the electronic medical invoice, wherein each next server application in the sequence is configured to process further the electronic medical invoice previously processed by the server application being in the sequence immediately before the each next server application in the sequence, wherein the last server application in the sequence is configured to execute reimbursement of medical costs according to the electronic medical invoice processed by the server applications of the sequence of the applications, and process the electronic medical invoice by the sequence of the server applications based on the collected user specific information and the one or more user specific rules, wherein the processing further includes extracting text data from the image by, identifying an area of the image that includes one or more graphical objects using a first pattern recognition method, generating an auxiliary image by subtracting the area of the image that includes the one or more graphical objects, and identifying the text data in the auxiliary image using a second pattern recognition method, wherein the electronic medical invoice is an electronic file including an image of a medical invoice printed on a substrate, the image is a mixed text/graphic image, one of the server applications in the sequence of the server applications is configured to extract text data from an image, the server includes a database storing graphical objects each associated with a respective text fragment, the database stores a plurality of sets of wavelet functions, the logic circuitry is further configured to cause the sequence of the server applications to process the electronic medical invoice by extracting text data from the image included in the electronic medical invoice, at least one of the server application is configured to extract the text data from the image included in the electronic medical invoice by, a) identifying the one or more graphical objects in the image using the first pattern recognition method, wherein the first pattern recognition method includes a feature extraction method in which features of each of the one or more graphical objects are extracted from the image using one set of wavelet functions of the plurality of sets of wavelet functions, b) identifying a set of graphical objects, wherein each of the graphical objects of the set of graphical objects is stored in the database and is identified in the last execution of b), c) in case when the set of graphical objects identified in the last execution of b) is empty repeating a) and b) until the set of graphical objects identified in the last execution of b) is not empty or all sets of the plurality of wavelet functions stored in the database are used in a), wherein in every next repetition of a) another not yet used in a) set of wavelet functions stored in the database is used, and d) in case when the set of graphical objects identified in the last execution of b) is not empty performing the following:

retrieving from the database a set of text fragments, wherein each of the text fragments of the set of text fragments is associated with the respective graphical object of the set of graphical objects identified in the last execution of b), generating an auxiliary image by subtracting from the image an image of the one or more graphical objects identified in the last execution of a), and identifying, using a second pattern recognition, text data in the generated auxiliary image, and e) in case when none of the text fragments of the set of text fragments retrieved from the database in the last execution of d) is included in the text data identified in the last execution of d), repeating a)-d) until one of the text fragments of the set of text fragments retrieved from the database in the last execution of d) is included in the text data identified in the last execution of d) or all sets of the plurality of wavelet functions stored in the database are used in a), wherein in every next repetition of a) another not yet used in a) set of wavelet functions stored in the database is used, wherein the text data extracted by the one of the server applications from the image included in the electronic medical invoice is the text data identified in d) when one of the text fragments of the set of text fragments is included in the text data identified in d).

2. The electronic payment system of claim 1, wherein each electronic medical invoice has a respective type;

the logic circuitry is configured to assign a respective customized sequence of the server applications of the set of the server applications for processing of each of the types;

the sequence of the server applications is one of the customized sequences of the server applications;

at least two of the customized sequences of the server applications have common fragments of the sequences of the server applications;

each of the customized sequences of the server applications begins with the respective receiver application for receiving and processing of the electronic medical invoices of the type for which the each of the customized sequences of the server applications is customized;

electronic medical invoices of one type have a text format;

electronic medical invoices of another type include images of medical invoices printed on carriers, and the electronic medical invoices of each of the types are received via digital cellular telecommunication networks by the server from respective sender applications for sending the electronic medical invoices of the each of the types.

3. The electronic payment system of claim 1, wherein each electronic medical invoice has a respective type;

the logic circuitry is configured to monitor a number of electronic medical invoices to be processed by the server applications of the sequence of the server applications;

one or more of the server applications of the sequence of the server applications are configured to process the electronic medical invoices in two modes, wherein in one mode of the two modes the electronic medical invoices are processed one by one and in another one of the two modes the electronic medical invoices of the same type are processed batch wise; and the logic circuitry is further configured to process electronic medical invoices in the another one of the two modes based on a number of electronic medical invoices of the same type to be processed by the server application being bigger than a predefined number otherwise the logic circuitry is configured to process the electronic medical invoices in the one of the two modes.

4. The electronic payment system of claim 1, wherein the logic circuitry is configured to, monitor a workload of the server application of the sequence of the server applications; and allocate hardware resources of the server for execution of the server applications; and allocate respective hardware resources of the server for execution of each of the server applications of the sequence of the server applications in conjunction with the respective work load of the each of the server application of the sequence of the server applications such that time required for processing of electronic medical invoices by the sequence of the server applications is minimized.

5. The electronic payment system of claim 1, wherein the server includes a database;

a processing application of the sequence of the server applications is operable for monitoring and managing work load of the processing application; and the logic circuitry is further configured to, split, in two portions, a set of electronic medical invoices to be processed by the logic circuitry based on a number of the electronic medical invoices of the set exceeding a predefined number, store, in the database, one of the two portions, process another one of the two portions, retrieve from the database the one of the two portions, and process the one of the two portions retrieved from the database after the another one of the two portions is processed by the processing application.

6. The electronic payment system of claim 1, wherein each electronic medical invoice is assigned to a respective user;

the logic circuitry is configured to process electronic medical invoices according to user specific rules; and the logic circuitry is further configured to, receive from an application of a health insurance provider a user specific rule assigned to a user, and cause a processing application of the sequence of the server applications to process the electronic medical invoices assigned to the user according to the user specific rules.

7. The electronic payment system of claim 6, wherein the logic circuitry is further configured to, send information for the reimbursement of the medical costs to the application of the health insurance provider;

update user specific rules on a basis of the information for the reimbursement of the medical costs, cause the application of the health insurance provider to receive the information for the reimbursement of the medical costs;

cause the application of the health insurance provider updating the user specific rule on a basis of the information for the reimbursement of the medical costs in response to the receiving of the information for the reimbursement of the medical costs; and receive the updated user specific rule from the application of the health insurance provider.

8. The electronic payment system of claim 6, wherein the logic circuitry causes the application of the health insurance provider to be executed by the server.

9. The electronic payment system of claim 1, wherein the logic circuitry is further configured to, cause the server applications to process the electronic medical invoice according to the one or more user specific rules;

assign the electronic medical invoice to the user;

receive from an application of a health insurance provider the one or more user specific rules assigned to the user;

determine processing of the electronic medical invoice in conjunction with the user specific information being descriptive of compliance with a health care plan based on the one or more user specific rules;

cause another receiver application of the set of the server applications to, receive the user specific information via the digital cellular telecommunication network from another sender application executed on the end terminal, convert the received user specific information in a data format being parsable by a processing application of the sequence of the server applications, and send the converted user specific information to the processing application;

receive from the another receiver application the converted user specific information, and process the electronic medical invoices assigned to the user based on the received converted user specific information and the one or more user specific rule.

10. The electronic payment system of claim 1, wherein the second pattern recognition method is a statistical pattern recognition method.

11. The electronic payment system of claim 1, wherein the first pattern recognition method includes a feature extraction method in which features of graphical object are extracted from the image using a set of wavelet functions.

12. The electronic payment system of claim 1, wherein the server includes a database storing graphical objects each associated with a respective text fragment; and the logic circuitry is further configured to cause the one of the server applications to extract the text data form the image included in the electronic medical invoice by, identifying a set of graphical objects, wherein each of the graphical objects of the set of graphical objects is stored in the database and is identified by identifying of the one or more graphical objects in the image using the first pattern recognition method, in case when the set of graphical objects is empty the one of the server applications sending an error message, otherwise retrieving from the database a set of text fragments, wherein each of the text fragments of the set of text fragments is associated with the respective graphical object of the set of graphical objects, wherein the identifying of the text data in the auxiliary image using the second pattern recognition method is executed when the set of graphical objects is not empty, and in case when none of the text fragments of the set of text fragments is included in the identified text data the one of the server applications sending the error message.

13. The electronic payment system of claim 12, wherein
the graphical objects stored in the database are logotypes of health care providers and the text fragments are company details of the health care providers; and
the logotype of each of the health care providers is associated in the database with the company details of the each of the health care providers.

14. The electronic payment system of claim 12, wherein the logic circuitry is further configured to respond to receiving the error message from the one of the server applications by:
aborting execution of extracting of text data form the image included in the electronic medical invoice;
halting execution of the sequence of the server applications processing the electronic medical invoice; or
sending a processing error message to the sender application.

15. The electronic payment system of claim 1, wherein
the electronic medical invoice includes a user identification information assigned to a user; and
the logic circuitry is further configured to,
configure another receiver application of the set of the server applications to,
receive, via a computer network from a sender application executed on an identity provider server, user credentials assigned to a user to whom the electronic medical invoice is deemed to be assigned,
convert the user credentials in a format parsable by a processing application of the sequence, and
end the converted user credentials to the processing application, and
configure the processing application to process electronic medical invoices assigned to the user by,
receive from the another receiver application the converted user credentials, and
send an error message based on the user identification information included in the electronic medical invoice and the received converted user credentials are not assigned to the same user.

16. A computer-implemented method for reimbursement of medical costs using an electronic payment system including a server operable for execution of an application management component and a set of server applications including receiver applications and processing applications, the computer-implemented method comprising:
receiving, by the server, via a digital cellular telecommunication network an electronic medical invoice assigned to a user from a sender application executed on an end terminal of a user, wherein the electronic medical invoice includes an image including mixed text and graphics;
causing, by logic circuitry of the server, the end terminal of the user to collect user specific information from one or more health care devices that provide health care to the user and/or one or more health monitoring devices that monitor the user, based on a specification of the user specific information according to one or more user specific rules for processing the electronic medical invoice;
assigning, by logic circuitry of the server, a sequence of server applications of the set of server applications to an electronic medical invoice, wherein an application being first in the sequence is a receiver application configured to receive and to process the electronic medical invoice;
configuring each next following server application in the sequence to process further the electronic medical invoice previously processed by the server application being in the sequence immediately before the each next following server application in the sequence, wherein further processing the electronic medical invoice includes extracting text data from the image by,
identifying an area of the image that includes one or more graphical objects using a first pattern recognition method,
generating an auxiliary image by subtracting the area of the image that includes the one or more graphical objects, and
identifying the text data in the auxiliary image using a second pattern recognition method;
configuring the last server application in the sequence is configured to execute reimbursement of medical costs according to the electronic medical invoice processed by the server applications of the sequence of the applications;
causing the sequence of the server applications to process the electronic medical invoice based on the collected user specific information and the one or more user specific rules, wherein
the electronic medical invoice is an electronic file including an image of a medical invoice printed on a substrate,
the image is a mixed text/graphic image,
one of the server applications in the sequence of the server applications is configured to extract text data from an image,
the server includes a database storing graphical objects each associated with a respective text fragment,
the database stores a plurality of sets of wavelet functions, and
the method further comprises,
causing the sequence of the server applications to process the electronic medical invoice by extracting text data from the image included in the electronic medical invoice, by:
a) identifying the one or more graphical objects in the image using the first pattern recognition method, wherein the first pattern recognition method includes a feature extraction method in which features of graphical objects are extracted from the image using one of the sets of the plurality of sets of wavelet functions,
b) identifying a set of graphical objects, wherein each of the graphical objects of the set of graphical objects is stored in the database and is identified in the last execution of b),
c) in case when the set of graphical objects identified in the last execution of b) is empty, repeating a) and b) until the set of graphical objects identified in the last execution of b) is not empty or all sets of the wavelet functions stored in the database are used in a), wherein in every next repetition of a) another not yet used in a) set of wavelet functions stored in the database is used,
d) in case when the set of graphical objects identified in the last execution of b) is not empty performing the following:
retrieving from the database a set of text fragments, wherein each of the text fragments of the set of text fragments is associated with the respective graphical object of the set of graphical objects identified in the last execution of b), generating an auxiliary image by subtracting from the image an image of the one or more graphical objects identified in the last execution of a), and identifying, using a second pattern recognition, text data in the auxiliary image, and e) in case when none of the text fragments of the set of text fragments retrieved from the database in the last execution of d) is included in the text data identified in the last execution of d), repeating a)-d) until one of the text fragments of the set of text fragments retrieved from the database in the last execution of d) is included in the text data identified in the last execution of d) or all sets of the plurality of wavelet functions stored in the database are used in a), wherein in every next repetition of a) another not yet used in a) set of wavelet functions stored in the database is used, wherein the text data extracted by the one of the server applications from the image included in the electronic medical invoice is the text data identified in d) when one of the text fragments of the set of text fragments is included in the text data identified in d).

17. A non-transitory computer readable medium having stored thereon computer executable code for execution by logic circuitry of an electronic payment system, wherein execution of instructions of the computer executable code by the logic circuitry causes the electronic payment system to execute the computer-implemented method of claim 16.

18. The electronic payment system of claim 1, wherein the one or more health care devices include one or more of a device for administration of medication and a massage device, and the one or more health monitoring devices include one or more of a blood pressure measurement device and a heart rhythm measurement device.

19. A computer-implemented method of claim 16, wherein the one or more health care devices include one or more of a device for administration of medication and a massage device, and the one or more health monitoring devices include one or more of a blood pressure measurement device and a heart rhythm measurement device.

* * * * *